(12) United States Patent
Zupančič et al.

(10) Patent No.: US 6,252,091 B1
(45) Date of Patent: Jun. 26, 2001

(54) PROCESS FOR THE PREPARATION OF SIMVASTATIN AND DERIVATIVES THEREOF

(75) Inventors: Silvo Zupančič, Novo mesto; Anton Stimac, Ljubljana; Jože Gnidovec, Novo mesto, all of (SI)

(73) Assignee: KRKA, Tovarna Zdravil, D.D., Nova mesto (SI)

( * ) Notice: Subject to any disclaimer, the term of this patent is extended or adjusted under 35 U.S.C. 154(b) by 0 days.

(21) Appl. No.: 09/668,101

(22) Filed: Sep. 22, 2000

Related U.S. Application Data

(63) Continuation of application No. PCT/SI99/00006, filed on Feb. 24, 1999.

(30) Foreign Application Priority Data

Feb. 26, 1998 (SI) .................................................. 9800057

(51) Int. Cl.[7] .................................................. C07D 309/30

(52) U.S. Cl. ........................................... 549/292; 549/214

(58) Field of Search ..................................... 549/214, 292

(56) References Cited

FOREIGN PATENT DOCUMENTS

| 0022 478 | 2/1983 | (EP) . |
|---|---|---|
| 0033 538 | 11/1985 | (EP) . |
| 0137 445 | 1/1990 | (EP) . |
| 0299 656 | 12/1990 | (EP) . |
| 0444 888 | 9/1991 | (EP) . |
| 0287 340 | 9/1993 | (EP) . |
| WO 93/16188 | 8/1993 | (WO) . |
| WO 97/05269 | 2/1997 | (WO) . |

OTHER PUBLICATIONS

J. Med. Chemistry 1986 vol. 29 pp. 859–852.
J. Org. Chemistry 1991 vol. 56 pp. 4929–4932.
Analytical Chemistry vol. 50 pp. 1542–1545.
Analytical Chemistry vol. 52 pp. 572–573.

*Primary Examiner*—Amelia Owens
(74) *Attorney, Agent, or Firm*—Cohen, Pontani, Lieberman & Pavane

(57) ABSTRACT

A process for the preparation of compounds of formula (I)

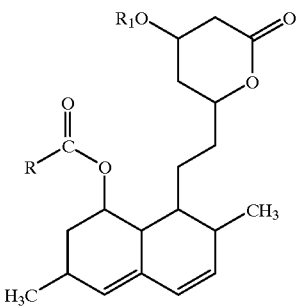

(I)

wherein
R is a $C_1$ to $C_{12}$ alkyl group and
$R_1$ is a protecting group or H
which process comprises
(a) converting the diol lactone of formula (II)

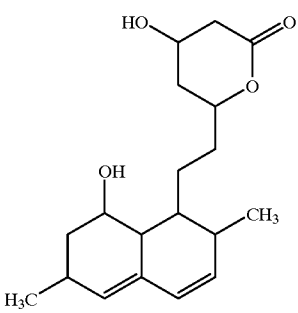

(II)

to the protected diol lactone of formula (IIa) wherein $R_1$ is a protecting group

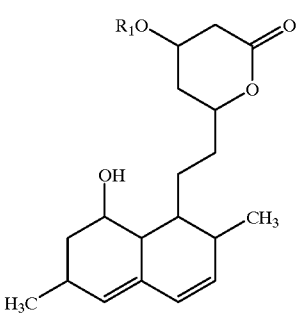

(IIa)

(b) acylating the protected diol lactone (IIa) to give compound (I) wherein $R_1$ is a protecting group,
(c) optionally removing the protecting group $R_1$ to give compound (I) wherein $R_1$ is H; and
wherein steps (a) and/or (b) are carried out in the presence of N-methylimidazole.

14 Claims, No Drawings

PROCESS FOR THE PREPARATION OF SIMVASTATIN AND DERIVATIVES THEREOF

CROSS-REFERENCE TO RELATED APPLICATION(S)

This application is a continuation of application No. PCT/SI99/100006—filed Feb. 24, 1999.

TECHNICAL FIELD OF THE INVENTION

The invention relates to a process for the preparation of the HMG-CoA-reductase inhibitor simvastatin and derivatives thereof.

Simvastatin is a semi-synthetic analog of the natural fermentation product lovastatin which has a 2-methylbutyrate side chain in the 8-position of the hexahydronaphthalene ring system. It has been discovered that the replacing of the 2-methylbutyrate group by a 2,2-dimethylbutyrate group results in more active inhibitors of HMG-CoA reductase (J. Med. Chem., 1986, 29(5), 849–852).

TECHNICAL PROBLEM

Heretofore, the preparation of simvastatin and derivatives thereof was only possible in low yield. The prior art processes also suffer from the drawback that large amounts of unconsumed starting materials remain after completion of the reaction. These starting materials as well as substantial amounts of undesired by-products formed during the process result in complications when recovering the product. Thus, there exists a need for a process overcoming theses problems.

BACKGROUND OF THE INVENTION

The known processes for preparing simvastatin and derivatives thereof can basically be divided according to two synthesis approaches used, namely (a) the so-called re-esterification route and (b) the direct methylation of the methyl butyrate side chain.

An example for the first synthetic approach is described in EP-B-33 538. It discloses a five-step process which comprises the steps of (1) exhaustive saponification of lovastatin; (2) relactonisation; (3) selective silylation; (4) re-acylation; and (5) desilylation. The reported overall yields obtained by this process are low, namely just 48% (J. Org. Chem 56, 4929 (1991)). This is partly attributable to the low yield of 69% obtained in the selective silylation step (3). Further, the re-acylation (4) is carried out at a high temperature of 100° C. for prolonged time (18–36 hours) in the presence of 4-pyrrolidino pyridine or dialkylamino pyridine. These reaction conditions lead to formation of a substantial amount of undesired by-product (unsaturated lactone) resulting from the elimination of the tert.-butyldimethylsilyloxy radical, present as protecting group of the alcohol, from the δ-valerolactone moiety. Finally, also large amounts of starting diol lactone and unconsumed acid chloride remain at the end of the reaction.

In EP-B-287340 an improved acylation process for the preparation of antihypercholesterolemic compounds is disclosed which comprises the combining of a suitable acid chloride with an alkali metal bromide, dialkylaminopyridine and a polyhydronaphthyl alcohol to obtain the corresponding acylated product. The reaction is carried out at a relatively high temperature of 70° C. so the unsaturated lactone by-product is also formed in an amount of about 1–2%. Moreover, the preferred solvent used in this process is pyridine which is environment and people unfriendly.

The second synthesis approach, the direct alkylation of the methyl butyrate side chain, is disclosed in EP-B-137 445 and EP-B-299 656. The processes involve use of a metal alkyl amide and methyl halide. The main disadvantage of these processes is the contamination of the product by a significant amount of unconverted starting materials, e.g. lovastatin. Since simvastatin and lovastatin differ only by one methyl group, it is very difficult to isolate simvastatin from a mixture containing both by means of conventional separation methods. Thus, an additional purification step is normally required, for example the selective hydrolysis of residual lovastatin as per the method disclosed in WO 93/16188.

N-methylimidazole, also referred to as 1-methylimidazole, is a known compound useful for the acetylation of hydroxy compounds with acetic anhydride (see Anal. Chem. 50, 1542–1545 (1978)). However, the reaction with sterically hindered alcohols gives only a poor yield. In case of tert.-butyl alcohol the yield is only 36%.

Moreover, in Anal. Chem. 52, 572 (1980) it is described that N-methylimidazole can also be employed as a catalyst for the acetylation of hydoxyl-terminated polymers by acetic anhydride.

DETAILED DESCRIPTION OF THE INVENTION

According to the invention a process for the preparation of compounds of formula (I)

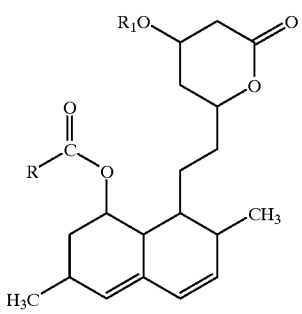

(I)

wherein
R is a $C_1$ to $C_{12}$ alkyl group and
$R_1$ is a protecting group or H
is provided which process comprises
(a) converting the diol lactone of formula (II)

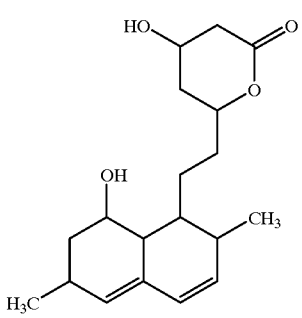

(II)

to the protected diol lactone of formula (IIa) wherein $R_1$ is a protecting group

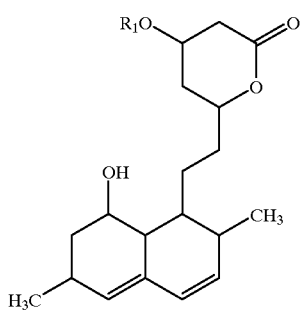

(IIa)

(b) acylating the protected diol lactone (IIa) to give compound (I) wherein $R_1$ is a protecting group, and (c) optionally removing protecting group $R_1$ to give compound (I) where $R_1$ is H, and wherein steps (a) and/or (b) are carried out in the presence of N-methylimidazole.

The compounds of formula (I) are effective antihypercholesterolemic compounds and include in particular simvastatin. In formula (I) the group R can be a $C_1$ to $C_{12}$ branched or straight alkyl group or a $C_3$ to $C_7$ cyclic alkyl group, preferably a $C_5$ alkyl group and in particular $CH_3$—$CH_1$—$C(CH_3)_2$—.

Suitable examples of protecting groups $R_1$ are groups conventionally used for selectively protecting hydroxy groups, such as silyl groups. Preferred are trialkyl silyl groups, such as isopropyldimethylsilyl, (triphenylmethyl) dimethylsilyl, tert.-butyldiphenylsilyl, methyldiisopropylsilyl, tribenzylsilyl, triisopropylsilyl and a particularly preferred example is the tert.-butyldimethysilyl group.

It was surprisingly shown that the compounds (I) can be prepared by the acylation process according to the invention in a very efficient manner and with high yield without formation of substantial amounts of undesired by-product. It was found that particularly good results are obtained if N-methylimidazole is present in both process step (a) and (b). Thus, N-methylimidazole seems to act as a catalyst not only for the protection step (a) but also for the acylation step (b) resulting in an excellent overall yield.

The diol lactone (II) used in step (a) is for example available by hydrolysation of lovastatin according to the method disclosed in EP-B-33 538.

In case of the introduction of a silyl group, such as the tert.-butyldimethyl silyl group, as a protecting group, the yield obtained in step (a) is virtually 100%. As practically no by-products are formed in step (a), it is possible to carry step (a) and (b) as a one-pot reaction without the need to isolate the formed protected diol lactone (IIa). This preferred embodiment of the invention greatly simplifies the preparation of the desired compound (I). It was also found out that due to the presence of N-methylimidazole the reaction time for completing (a) is decreased and is normally only 1.5 to 4 h.

The N-methylimidazole is preferably used in an amount sufficient to dissolve at the chosen reaction temperature the diol lactone (II) and the protected diol lactone (IIa), respectively. It therefore can also serve as a solvent. Due to the possibility of employing it in step (a) and (b) there is no necessity to change the solvent after completion of step (a) which is very advantageous when carrying out a one-pot synthesis.

In contrast to prior art processes steps (a) and/or (b) can be carried out at low temperatures and in particular in the range of about 0 to about 30° C. The low reaction temperature especially when conducting the acylation reaction (b) results in a substantial reduction of the level of by-products, such as unsaturated lactone by-product. In the prior art methods the acylation step requires temperatures of 100° C. or 70° C.

The acylating step (b) is preferably carried out by reacting the protected diol lactone (IIa) with a suitable activated form of the acid of formula (III)

R—CO—OH (III)

Preferred activated forms are the corresponding acid anhydrides or acid halogenides. Particularly suitable are acid chlorides. The acid halogenides or acid anhydrides are commercially available compounds or can be prepared from known starting materials utilising standard chemical transformations.

It was surprisingly found out that the work-up of the reaction mixture obtained after completing the acylation reaction in (b) is facilitated to a great extent by the adding of a $C_1$- aliphatic alcohol, in particular methanol, to the mixture. It is assumed that the alcohol reacts with unconverted activated acid (III) under formation of the corresponding ester which can more easily be removed.

In the optional step (c) of the present process, the protecting group $R_1$ is removed by conventional means to give the corresponding compound of formula (I) where $R_1$ is H, such as simvastatin. For example the silyl protecting groups can be split off by using tetrabutylammonium fluoride/acetic acid and a corresponding procedure is described in EP-B-33 538, or by using boron trifluoride etherate as is disclosed in EP-A-444 888.

A preferred manner to carry out the present process is illustrated by the following reaction sequence starting with lovastatin:

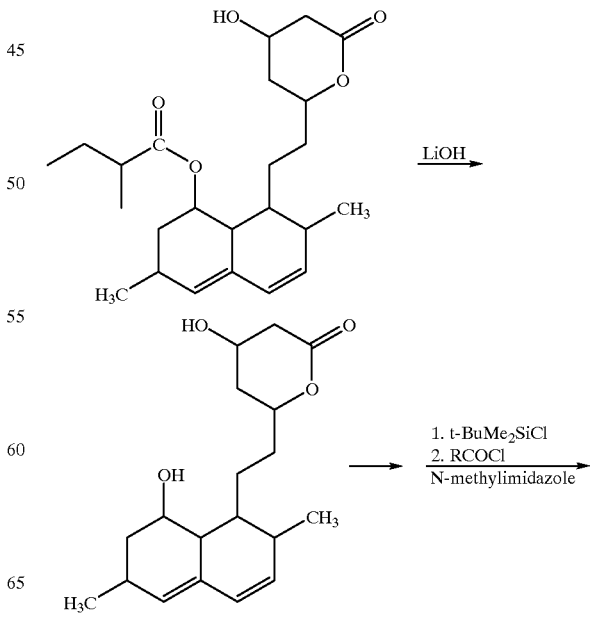

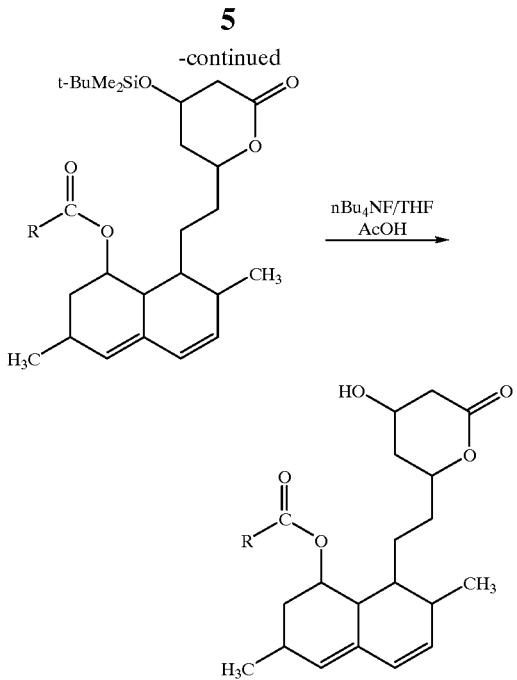

The lovastatin used in this sequence as starting material is commercially available or can be prepared by known processes, e.g. those described in EP-B-22 478 or WO 97/05269. In the first stage lovastatin is hydrolysed under the conditions disclosed in EP-B-33 538 to give the diol lactone (II). After introducing the silyl protecting group and acylation in the presence of N-methylimidazole the corresponding compound (I) is formed. This can optionally be converted in the deprotected compound (I) wherein $R_1$ is H by treatment with tetrabutylammonium fluoride/acetic acid in tetrahydrofuran.

The major advantages of the present process compared with the known processes are the higher yields of product (I), typically 90 to 95% (based on diol lactone (II)), the reduced amount of by-products, the possibility to carry out the reaction as a one-pot reaction and the ease of removing an excess of acylating agent when adding an alcohol to the reaction mixture.

EXAMPLES

In the examples content determination is performed by a HPLC analysis.

Example 1

Preparation of 6(R)-[2[8(S)-(2,2-dimethylbutyryloxy)-2(S),6(R)-dimethyl-1,2,6,7,8,8a(R)-hexahydronaphtyl-1(S)]ethyl]-4(R)-tert-butyldimethylsilyloxy-3,4,5,6-tetrahydro-2H-pyran-2-one 1.81 g (12 mmol) tert.-butyldimethylchlorosilane were added to a solution of 3.2 g (10 mmol) of the corresponding diol lactone of formula (II) in N-methylimidazole, and the mixture was stirred at room temperature for 3.5 h under a nitrogen atmosphere. The resulting solution was cooled to 0° C. and 5.5 ml (39 mmol) of 2,2-dimethylbutyryl chloride were added over a period of 20 minutes. The mixture was stirred at 0° C. for 1 h and then for 42 h at room temperature. 7 ml of methanol were added and it was stirred for 1 h. The obtained mixture was diluted with 250 ml of butyl acetate and washed with 0.07% HCl (300 ml) and saturated NaCl solution (2×125 ml). The combined organic phases were dried over anhydrous $MgSO_4$, filtered and volatile components were evaporated in vacuum to give the title compound as a light brown oil.

$^1$H-NMR (300 MHz, $CDCl_3$) in ppm (main peaks): 5.97 (d, 1H, J=9, 75 Hz), 5.75, (dd, 1H, J=9, 75, 6.15 Hz), 5.43–5.52 (m, 1H), 5.26–5.35 (m, 1H), 4.48–4.64 (m, 1H), 4.22–4.33 (m, 1H), 2.17–2.65 (m, 5H), 0.70–2.05 (m, 35H; containing two 3H singlets at 1.11 and a 9H singlet at 0.85 ppm), 0.06 (s,3H), 0.05 (s,3H).

The purity of the product determined by HPLC was 97–98.5 area %. The level of unsaturated by-product was under 0.5%. The content of the product was 93%.

The formed compound can be converted into simvastatin by removing the silyl protecting group in a conventional manner.

Example 2 (Comparative Example)

To show the superiority of the process according to the invention, the prior art method as is disclosed in example 2 of EP-B-287 340 was repeated.

Preparation of 6(R)-[2[8(S)-(2,2-dimethylbutyryloxy)-2(S),6(R)-dimethyl-1,2,6,7,8,8a(R)-hexahydronaphtyl-1(S)]ethyl]-4(R)-tert-butyldimethylsilyloxy-3,4,516-tetrahydro-2H-pyran-2-one Lithium bromide (2.08 g, 12 mmol, anhydrous, dried 4 days at 135° C. in vacuum) was added as rapidly as possible to a solution of 2,2-dimethylbutyryl chloride (1.62 ml, 12 mmol) in anhydrous pyridine (7 ml) under $N_2$. When the temperature returned to 25° C., a solution of the corresponding silyl-protected diol lactone (2.604 g, 6 mmol) and 4,4-dimethylaminopyridine (0.147 g, 1.2 mmol) in pyridine (7 ml) was added. The mixture was stirred at 70° C. for 3.5 h. The mixture was then cooled to room temperature, poured into $H_2O$ (70 ml) and extracted with 2×70 ml of ethyl acetate. The combined organic extracts were washed with 2×35 ml 1,2N HCl, 35 ml of saturated $NaHCO_3$ solution, 35 ml of saturated NaCl solution, dried over anhydrous $Na_2SO_4$, filtered and evaporated in vacuum to give the title compound as a light brown oil.

$^1$H-NMR (300 MHz, $CDCl_3$) in ppm (main peaks): 5.97 (d, 1H, J=9.75 Hz), 5.75 (dd, 1H, J=9.75, 6.15 Hz), 5.43–5.52 (m, 1H), 5.26–5.35 (m, 1H), 4.48–4.64 (m, 1H), 4.22–4.33 (m, 1H), 2.17–2.65 (m,5H), 0.70–2.05 (m, 35H; containing two 3H singlets at 1.11 and a 9H singlet at 0.85 ppm), 0.06 (s,3H), 0.05 (s,3H).

The purity of the product determined by HPLC was only 83 area % and the level of unsaturated by-product was 0.7%. Further 12% of the corresponding protected diol lactone (formula (IIa)) were detected indicating that the acylation reaction was by no means proceeding in a satisfactory manner.

What is claimed is:

1. A process for the preparation of compounds of formula (I)

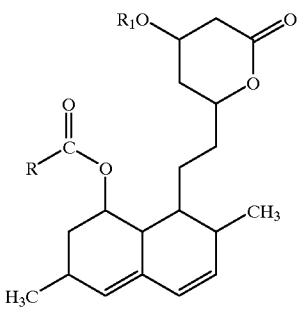

wherein
R is a $C_1$ to $C_{12}$ alkyl group and
$R_1$ is a protecting group or H
which process comprises
(a) converting the diol lactone of formula (II)

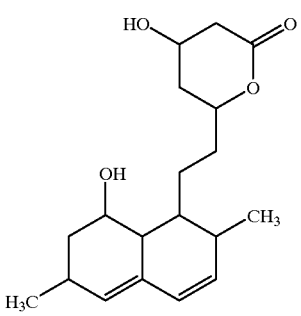

to the protected diol lactone of formula (IIa) wherein $R_1$ is a protecting group

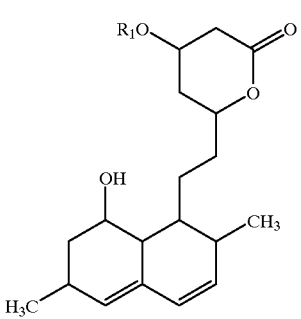

(b) acylating the protected diol lactone (IIa) to give compound (I) wherein $R_1$ is a protecting group, (c) optionally removing the protecting group $R_1$ to give compound (I) wherein $R_1$ is H; and wherein steps (a) and/or (b) are carried out in the presence of N-methylimidazole.

2. The process according to claim 1, wherein the N-methylimidazole is used in an amount sufficient to dissolve at the reaction temperature the diol lactone (II) and the protected diol lactone (IIa).

3. The process according to claim 1, wherein the protecting group $R_1$ is a silyl group.

4. The process according to claim 1, wherein the protecting group $R_1$ is a trialkyl silyl group.

5. The process according to claim 1, wherein tert.-butyldimethylsilyl is used as protecting group $R_1$.

6. The process according to claim 1, wherein in step (b) the protected diol lactone (IIa) is acylated with an activated form of the acid of formula (III)

R—CO—OH    (III)

and R is as defined in claim 1.

7. The process according to claim 6, wherein an acid halogenide of formula (IIIa)

R—CO-halogen    (IIIa)

or acid anhydride of formula (IIIb)

(R—CO)$_2$O    (IIIb)

is used as activated form of the acid (III).

8. The process according to claim 7, wherein an acid chloride is used as an acid halogenide.

9. The process according to claim 1, wherein after completion of step (b) a $C_{1-8}$ aliphatic alcohol, is added to the reaction mixture.

10. The process according to claim 9, wherein methanol is used as the aliphatic alcohol.

11. The process according to claim 1, wherein steps (a) and (b) are carried out as a one-pot reaction without isolating the protected diol lactone (IIa).

12. The process according to claim 1, wherein steps (a) and/or (b) are carried out at a temperature of about 0° to about 30° C.

13. The process according to claim 12, wherein R is a $C_5$ alkyl group.

14. The process according to claim 1, wherein the $C_5$-alkyl group is $CH_3$—$CH_2$—$C(CH_3)_2$.

* * * * *